United States Patent
Clay et al.

(10) Patent No.: US 11,400,389 B2
(45) Date of Patent: Aug. 2, 2022

(54) *MARSDENIA CUNDURANGO* CREEPER EXTRACTS, COSMETIC COMPOSITIONS COMPRISING THEM AND COSMETIC USES OF SAME

(71) Applicants: ISP Investments LLC, Wilmington, DE (US); JAFER ENTERPRISES R&D, S.L. (SOCIEDAD UNIPERSONAL), Barcelona (ES)

(72) Inventors: Anne Clay, Sant Just Desvern (ES); Nouha Domloge, Opio (FR); Isabelle Imbert, Cannes (FR); Karine Cucumel, Opio (FR); Esmeralda Cicchetti, Castets (FR); Ludivine Mur, Pegomas (FR); Garnier Sébastien, Le Rouret (FR); Leslie Duroure, Mouans Sartoux (FR)

(73) Assignees: ISP Investments LLC, Wilmington, DE (US); JAFER ENTERPRISES R&D, S.L. (SOCIEDAD UNIPERSONAL), Barcelona (ES)

( * ) Notice: Subject to any disclaimer, the term of this patent is extended or adjusted under 35 U.S.C. 154(b) by 396 days.

(21) Appl. No.: 16/484,784

(22) PCT Filed: Feb. 6, 2018

(86) PCT No.: PCT/EP2018/052887
§ 371 (c)(1),
(2) Date: Aug. 8, 2019

(87) PCT Pub. No.: WO2018/146066
PCT Pub. Date: Aug. 16, 2018

(65) Prior Publication Data
US 2021/0275939 A1    Sep. 9, 2021

(30) Foreign Application Priority Data

Feb. 9, 2017  (FR) ...................... 1770125

(51) Int. Cl.
*B01D 11/02* (2006.01)
*A61K 8/63* (2006.01)
(Continued)

(52) U.S. Cl.
CPC ............ *B01D 11/0203* (2013.01); *A61K 8/63* (2013.01); *A61K 8/9789* (2017.08); *A61Q 19/08* (2013.01);
(Continued)

(58) Field of Classification Search
None
See application file for complete search history.

(56) References Cited

FOREIGN PATENT DOCUMENTS

| CN | 105535515 A | 5/2006 |
|----|-------------|--------|
| JP | 3754025 B2 | 8/2006 |

OTHER PUBLICATIONS

The Southern Pharmaceutical Journal, vol. 7, Jan. 1914, pp. 273-274. (Year: 1914).*

(Continued)

*Primary Examiner* — Kyung S Chang
(74) *Attorney, Agent, or Firm* — William J. Davis; Nathalie Tietcheu

(57) ABSTRACT

The invention relates to a method for obtaining a *Marsdenia cundurango* extract containing terpinyl cinnamate compounds, the *Marsdenia cundurango* bark or wood extracts comprising terpinyl cinnamate compounds obtained by the method, cosmetic compositions comprising them, and the cosmetic uses of same for improving the barrier function of the skin, for improving protection against toxins and detoxification of the skin, and finally for reducing the signs of ageing.

13 Claims, 2 Drawing Sheets

(51) Int. Cl.
    *A61K 8/9789* (2017.01)
    *A61Q 19/08* (2006.01)

(52) U.S. Cl.
    CPC .... *B01D 11/0288* (2013.01); *A61K 2800/805* (2013.01)

(56) References Cited

OTHER PUBLICATIONS

Vincience Biofunctionals 2017 Brochure ([retrieved from on-line website: https://www.ashland.com/file_source/Ashland/Industries/Personal%20and%20Home%20Care/Articles/PC-12152.11_Vincience.pdf, 2017]). (Year: 2017).*

* cited by examiner

MARSDENIA CUNDURANGO CREEPER EXTRACTS, COSMETIC COMPOSITIONS COMPRISING THEM AND COSMETIC USES OF SAME

CROSS-REFERENCE TO RELATED APPLICATIONS

This application is a U.S. National Phase filing under 35 U.S.C. § 371 of International Application No. PCT/EP2018/052887, filed Feb. 6, 2018, and published as WO 2018/146066 A1 on Aug. 16, 2018, which claims benefit of priority French Patent Application No. 1770125 filed Feb. 9, 2017. The entire contents of each of the prior applications are incorporated herein by reference in their entirety.

The invention relates to a *Marsdenia cundurango* creeper bark and/or wood extract, preparation method for same, cosmetic compositions comprising them, and cosmetic uses of same.

Within the scope of the present invention, the plant in question is a climbing creeper, the botanical name of which is *Marsdenia cundurango* Rchb. F. and which belongs to the Apocynaceae family. This plant grows to between 2000 and 3000 metres tall. Also known as condurango, it originates from South America: it grows on the Western side of the Andes mountain range (at the Equator, in Peru and in Columbia). Condurango is a creeper with hairy branches. The trunk reaches a diameter of 10 cm. Young climbing shoots are covered by a thin soft coating; older branches and the trunk are encased in a grey bark. The latex produced by the plant is poisonous in its fresh state. The leaves of condurango, which are elongate and heart-shaped, are tough and downy. The small, greenish-white flowers grow in umbrella-shaped panicles in the axils of the leaves. The bark of condurango used as active substance originates from cultivated bushes. The active substance, called "condurango bark" (in Latin: condurango cortex) is in fact the dried bark of the branches and of the trunk of the plant. Transformed into a fine powder, the bark of condurango is used directly as a medicament. Cut finely or milled roughly, it is used as a basis for the preparation of infusions, extracts (for example Condurango extractum fluidum) or wine (condurango vinum). This remedy is bitter and a minor irritant. It is composed in particular of the bitter substance condurangine (a mixture of a number of glucosides), small amounts of flavonoids, and coumarin.

The part of the plant used in the present invention is the bark and/or the wood (branch and trunk) of the creeper.

Literature reviews disclose a certain number of compounds produced from the bark of *Marsdenia cundurango* (referred to hereinafter as "condurango"). A large proportion of isolation studies performed on this topic have revealed compounds of the condurangoside or condurangoglycoside type (Berger, S. et al., Structural Revision of Pregnane Ester Glycosides from Condurango Cortex and New Compounds. Phytochemistry 1988, 27 (5), 1451-1458; Umehara, K. et al., Studies on Differentiation Inducers. IV. Pregnane Derivatives from Condurango Cortex. Chem. Pharm. Bull. (Tokyo) 1994, 42, 611-616; Tschesche, R. et al. Digitanol Glycosides. XVI. Structure of Kondurangogenins A and C2. Tetrahedron 1967, 23, 1461-1471).

However, the bark of condurango has a notable chemical diversity because other families of secondary metabolites are also described in the literature. The presence of certain flavonoids such as rutin, quercitrin, hyperin, trifolin; some phenyl propanoids, such as chlorogenic, neochlorogenic and caffeic acids; or vanillin and a derivative of saponarin has been reported in the barks (Koch, H. et al. Components of Condurango Bark. 2. Pharm. Acta Helv. 1982, 57, 211-214. Condurangamines A and B have also been isolated and described in a study on this topic (Kindl, H. et al., Biosynthesis of Cyclitols. XIII. Occurrence and Biosynthesis of Cyclitols in Asclepiadaceae. Phytochem. Elsevier 1966, 5, 1091-1102).

It is additionally known, from a technical report on *Marsdenia cundurango* compiled by Dr. Taylor in 2006 (Taylor, L. Technical Data Report for Condurango (*Marsdenia cundurango*). 2006) that the plant comprises numerous compounds. Among the numerous known cited compounds in *Marsdenia cundurango*, this technical report cites in particular β-amyrin cinnamate present in the bark and the wood. The report clearly states that the plant was firstly used by the local populations to solve digestion-related problems and that it has also been included in some pharmacopoeias.

Thus, nowadays, among the known biological activities of condurango, reference can also be made to its anti-oxidant and anti-inflammatory properties (de las Heras, B. Et al., Antiinflammatory and Antioxidant Activity of Plants Used in Traditional Medicine in Ecuador. J. Ethnopharmacol. 1998, 61 (2), 161-166).

More recently, anti-cancer potential of condurango has been demonstrated by a number of teams. Sikdar et al. worked together to demonstrate the activity of a general extract of condurango, then of a glycosyl ester of condurangogenin A against lung cancer (Sikdar, S. et al., Anti-Lung Cancer Potential of Pure Esteric-Glycoside Condurangogenin A against Nonsmall-Cell Lung Cancer Cells in Vitro via p21/p53 Mediated Cell Cycle Modulation and DNA Damage-Induced Apoptosis. Pharmacogn. Mag. 2015, 11, 73-85; Sikdar, S. et al. Condurango Glycoside-Rich Components Stimulate DNA Damage-Induced Cell Cycle Arrest and ROS-Mediated Caspase-3 Dependent Apoptosis through Inhibition of Cell-Proliferation in Lung Cancer, in Vitro and in Vivo. Environ. Toxicol. Pharmacol. 2014, 37, 300-314; Sikdar, S. et al., Ethanolic Extract of *Marsdenia condurango* Ameliorates Benzo[a]pyrene-Induced Lung Cancer of Rats: Condurango Ameliorates BaP-Induced Lung Cancer in Rats. J. Pharmacopuncture 2014, 17, 7-17).

For their part, Bishayee et al. also demonstrated that condurango glycoside A can have an anti-cancer potential (Bishayee, K. et al., Condurango-Glycoside-A Fraction of Gonolobus Condurango Induces DNA Damage Associated Senescence and Apoptosis via ROS-Dependent p53 Signalling Pathway in HeLa Cells. Mol. Cell. Biochem. 2013, 382, 173-183).

Lastly, epigenetic studies have been carried out very recently (Saha et al., Ultra-Highly Diluted Plant Extracts of Hydrastis Canadensis and *Marsdenia condurango* Induce Epigenetic Modifications and Alter Gene Expression Profiles in HeLa Cells in Vitro. J. Integr. Med. 2015, 13, 400-411).

The applicants have now developed a new extraction method applied to the bark and/or wood of dried condurango creeper, making it possible to obtain an extract that is rich in terpinyl cinnamate compounds and that has a range of cosmetic activities not described previously.

Thus, the extract of condurango according to the present invention has proven to be useful for improving the barrier function of the skin, for improving protection of the skin against toxins, for improving detoxification of the skin, and for reducing the signs of ageing. The applicants have also demonstrated the ability of the *Marsdenia cundurango* creeper bark and/or wood extract to increase the expression of bitter taste receptors (TAS2R) in the cells of the skin. This family of receptors, and in particular the receptor TAS2R38, which has been identified in skin cells, is activated by different plant metabolites and certain synthetic chemical substances. The activation of this receptor is linked to an improvement in the skin barrier function (Walfle U et al. Expression and functional activity of the bitter taste receptors TAS2R1 and TAS2R38 in human keratinocytes. Skin Pharmacol Physiol. 2015; 28(3):137-46).

In the cosmetic field, a document referring to the *Marsdenia* genus in its entirety is known; specifically document JP3754025 by Noevir. This document describes the use of a plant extract of the *Marsdenia tenacissima* genus as an antioxidant agent for preventing ageing of the skin. It states that the entire plant should be used, and the examples confirm an extraction from the whole plant, in particular the roots, the leaves, the stem, the wood and the flowers. The extraction method uses water and alcohols and can also use a supercritical fluid, in this case without addition of co-solvent, moreover under application of a pressure of 15 MPa and a temperature of 40° C.

The extraction method according to the present invention, developed by the applicants and performed specifically on the bark and/or wood of condurango creeper, is novel over the documents cited above. The method is optimised to select and guarantee in the obtained extract an elevated level of target molecules of interest, that is to say terpinyl cinnamate compounds.

The compounds of interest are, in accordance with the invention, the following terpinyl cinnamate compounds:

β-amyrin cinnamate, of following formula:

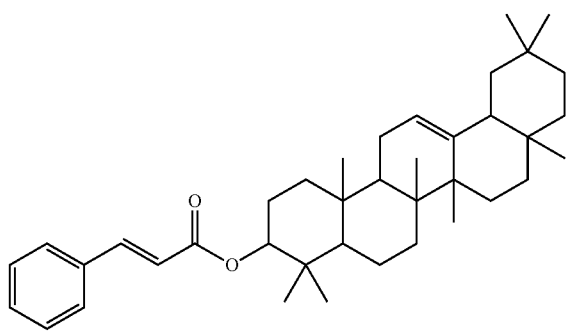

24-methylene cycloartanyl cinnamate,

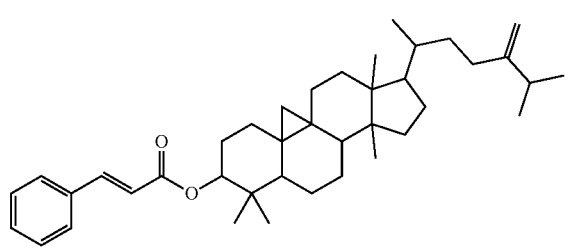 [SMILES: C=C(CCC(C)C1CCC2(C)C3CCC4C(C)(C)C(OC(=O)/C=C/c5ccccc5)CCC45CC35CCC12C)C(C)C]

butyrospermyl cinnamate, of following formula:

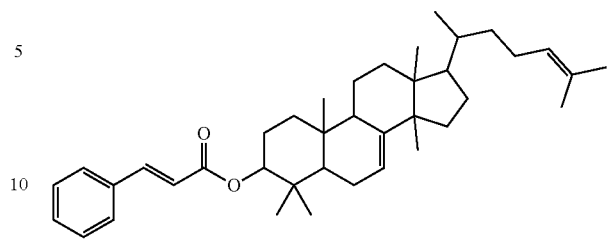

cycloartenyl cinnamate, of following formula:

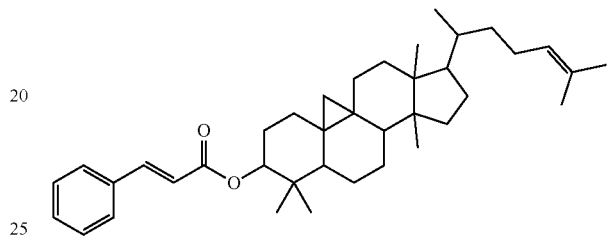

and,
cyclofontumienyl cinnamate, of following formula:

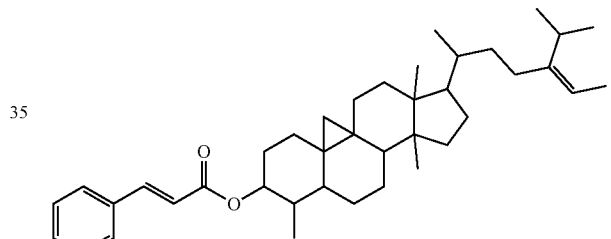

24-methylene cycloartanyl cinnamate and cycloartenyl cinnamate are references in the works by Lai et al. on the fruit of *Gymnema alternifolium* detailing an antimicrobial activity (Lai, J. S. et al., Studies on the Constituents of the Fruits of *Gymnema alternifolium* (Lour.) Merr. Proc. Natl. Sci. Counc. Repub. China Part Phys. Sci. Eng. 1987, 11, 203-208).

For the butyrospermyl cinnamate compound, the publication by Akihisa et al. discusses the anti-inflammatory and anti-tumour potential of the triterpene acetates and cinnamates of Shea butter (Akihisa, T. et al., Anti-Inflammatory and Chemopreventive Effects of Triterpene Cinnamates and Acetates from Shea Fat. J. Oleo Sci. 2010, 59, 273-280).

It is also known from a precis dating from 1942 that β-amyrin cinnamate is present in the bark of condurango (Kern, W.; Haselbeck, W. Components of Condurango Bark. IV. Arch. Pharm. Ber. Dtsch. Pharm. Ges. 1942, 280, 277-292) but does not make any mention of its biological potential. The digestive biological potential is described in the above-cited technical report on *Marsdenia cundurango* compiled by Dr. Taylor in 2006 (Taylor, L. Technical Data Report for Condurango (*Marsdenia cundurango*).

Nevertheless, hitherto it was neither known nor suggested that the bark and/or the wood of condurango could contain an elevated level of target molecules of interest according to the invention, i.e. the different terpinyl cinnamates. It was neither known nor suggested that the specific extraction method implemented in accordance with the present invention can make it possible to select and to concentrate the compounds of interest according to the invention from the bark and/or wood of condurango.

The invention therefore relates firstly to a method for producing a *Marsdenia cundurango* extract comprising terpinyl cinnamate compounds, characterised in that said method comprising the following steps:
a) the bark and/or wood of *Marsdenia cundurango* creepers are/is collected, dried and then milled;
b) an extraction is performed with a fluid in the supercritical state;
c) the *Marsdenia cundurango* extract is recovered,
d) the extract obtained in step c) possibly is purified.

The invention relates secondly to an extract originating from the bark and/or wood of the *Marsdenia cundurango* creeper containing terpinyl cinnamate compounds obtained by the method above.

The invention relates thirdly to a cosmetic composition comprising, as active agent, an effective amount of a *Marsdenia cundurango* extract obtained by the method above and a physiologically acceptable excipient.

The invention relates fourthly to the cosmetic use of a composition for improving the barrier function of the skin, for improving protection against toxins, for increasing the detoxification capabilities of the skin, and for reducing the signs of ageing.

Lastly, the invention relates fifthly to a cosmetic treatment method for increasing the expression of bitter taste receptors in the cells of the skin, comprising topical application of a composition of the invention.

In this description, unless specified otherwise in the text, it shall be understood that:
when a range is given, said range includes the upper and lower limits of said range as well as the numerical values between the range limits;
the % are expressed in the text as weight/weight or mass %, unless stated otherwise.

In the present invention:
"effective amount" means the amount of condurango extract necessary to obtain the sought result, that is to say in particular the amount making it possible to obtain cutaneous protection against toxins or an increase in the expression of the marker TAS2R, without this amount being toxic.
"condurango extract", "*Marsdenia cundurango* creeper extract" or "*Marsdenia cundurango* extract" can be used synonymously and denote an extract originating from the bark and/or wood of the *Marsdenia cundurango* plant, obtained by the method of the invention.
"bark and/or wood" means the bark surrounding the branches and the trunk of the plant and/or the wood (branches and trunk of the plant).
"molecules of interest" means the terpinyl cinnamate compounds and apolar molecules extracted by the method according to the invention.
apolar co-solvent: non-polar substance playing the role of solvent in combination with another substance
fluid in the supercritical state: physical state of a pure body heated beyond its critical temperature and compressed beyond its critical pressure. (examples: carbon dioxide or argon).
"terpinyl cinnamate" the compounds of the family of triterpenes or steroids esterified in position 3 by cinnamic acid.
"topical application" means the fact of applying or spreading the active agent according to the invention, or a composition containing same, to the surface of the skin, a mucous membrane or the appendages.
"toxin" means not only the toxic substances produced by living organisms, such as bacteria, fungi or venomous animals, but also chemical and environmental pollutants which can come into contact with the skin and cause damage.
"chemical and environmental pollutants" means the pollutants present in the environment which are harmful to the skin. They can be present both outdoors, for example diesel engine particles, ozone, or heavy metals, and/or indoors inside homes, where the pollution can be caused in particular by cigarette smoke or solvents released by paints, glues or wallpapers, such as toluene, styrene, xylene, benzaldehyde.
"detoxification" that the condurango extract improves the ability of the skin to detect and to eliminate waste products in order to achieve improved function.
"cosmetically acceptable" means that the compounds of interest or the active agent according to the invention, or a composition containing same, is suitable for coming into contact with the skin or a mucous membrane without provoking any reactions of toxicity or intolerance.
"physiologically acceptable" means suitable for topical use, in contact with the human skin, or for use by other administration methods, for example orally or by way of injection into the skin, without risk of toxicity, incompatibility, instability, or allergic reaction.
"signs of skin ageing" means any modification of the outer appearance of the skin caused by chronological ageing, such as wrinkles and fine lines, creases, bags under the eyes, dark circles, sagging, loss of elasticity and/or skin tone, dulling or lack of radiance, pigment deficiencies, but also any internal modification of the skin which is not manifested systematically in the form of a modified external aspect, such as a reduction and loss of density of the dermis, thickening of the stratum corneum. The skin may also thicken and become rough. The signs of ageing also include any degradation of the skin following exposure to UV rays, such as the premature appearance of fine lines around the eyes and the mouth, and expression lines on the face; telangiectasia (small dilated blood vessels) on the nose, the cheeks and the neck, different areas of pigmentation, such as freckles and solar lentigines, irregularities in the complexion, generalised loss of tone of the skin, loss of colour and thinning of the lips. What is also meant is any internal modification of the skin which does not manifest itself systematically in the form of a modified external aspect, for example the thickening of the vessel walls, the modification of the shape of the fibroblasts, the slowing of collagen synthesis and a disorganisation of collagen fibrils, an accumulation of abnormal and amorphous material containing elastin (solar elastosis).

The signs of skin ageing also manifest at molecular and cellular level, for example by the slowing of autophagy, a lysosomal degradation pathway allowing the elimination of toxins and of intercellular components. Chaperone-mediated autophagy (CMA) is one of the selective forms of autophagy, characterised by the presence of LAMP2A. The level of LAMP2A in the lysosomal membrane decreases with age, resulting in a failure of CMA activity (E. Bejarano et A. M. Cuervo, Chaperone-mediated Autophagy, Proc Am Thorac Soc, Vol 7, 29-39, 2010 et S. Kaushik, U. Bandyopadhyay, S. Sridhar, R. Kiffin, M. Martinez-Vicente, M. Kon, S. J. Orenstein, E. Wong, A. M. Cuervo, Chaperone-mediated autophagy at a glance, Journal of Cell Science 124, 495-499, 2011).

The invention therefore relates firstly to a method for obtaining a *Marsdenia cundurango* extract containing terpinyl cinnamate compounds.

In order to obtain this apolar *Marsdenia cundurango* extract containing terpinyl cinnamate compounds, it is possible to use a number of methods, such as:

1) Conventional Solid/Liquid Extraction by an Apolar Solvent:

Solid-liquid extraction is an operation in which substances are transferred between the "solid" material and a "liquid" extraction solvent, for which these substances have a polarity affinity. The solvent used will be a volatile or non-volatile apolar solvent.

2) Extraction Assisted by Microwaves and/or by Ultrasound:

In contrast to the conventional techniques of heating by conduction or convection, the use of microwaves involves direct interaction between electromagnetic radiation and the material. Heating a product by microwaves thus results in the conversion of the energy from an electromagnetic wave into heat within this material. This particular transfer of energy induces a material transfer, which is also distinctive, and therefore different mechanisms, in particular those of traditional solid-liquid extraction.

The efficacy (in terms of yield or kinetic extraction) and selectivity (in terms of purity of the products) of extraction methods assisted by microwaves are a consequence of these particular conditions of material and energy transfer.

The durations of extraction methods assisted by microwaves are of the order of a few minutes. It is potentially of interest to couple the action of the microwaves with apolar solvents, preferably non-volatile apolar solvents.

The use of ultrasound also makes it possible to improve the phenomena of destruction of plant cells by cavitation and diffusion of the molecules of interest in the solvent. This makes it possible to increase the yield, decrease the amount of solvent required and/or the treatment time. The action of the ultrasound is preferably realised in the presence of non-volatile apolar solvents. It is also potentially of interest to couple the action of the ultrasound with the action of microwaves in the presence preferably of non-volatile apolar solvents.

3) Extraction Assisted by Pulsed Electrical Fields:

The treatment by pulsed electrical fields is a selective non-thermal treatment of very short duration, generally lasting a few microseconds to a few milliseconds.

When the applied pulsed electrical fields exceed a critical value, the cellular membranes are destroyed irreversibly, which considerably improves the efficacy of the methods and the quality of the extract products.

4) Extraction by Supercritical Fluid:

A fluid said to be supercritical when it is placed under temperature and pressure conditions beyond its critical point ($T_c$, $P_c$). The physical properties of a supercritical fluid (density, viscosity, diffusion, diffusivity) lie between those of liquids and those of gases, but their properties of dissolution are considerably increased. It is well known to use carbon dioxide ($CO_2$) in the supercritical state because it has the advantage of being a completely neutral, non-toxic, non-flammable solvent, which can be used at a quite low temperature (31° C.) for a pressure greater than its critical pressure of 73.8 bar. This technique makes it possible to work at a moderate temperature (from 31° C.), which does not adversely affect the organoleptic qualities and the active ingredients of the obtained extract. In addition, after the evaporation of the CO2 returned to the gaseous state, it is possible to obtain extracts exempt of all residues of the extraction solvent. It is also possible to use other fluids, in particular argon.

5) Extraction by Subcritical Water:

Extraction by subcritical water or pressurised hot water is used at temperatures between 100° C. (boiling point of water) and 374.1° C. (critical point of water), and the water is maintained in its liquid form under the effect of strong pressures. Water at ambient temperature is a polar solvent. However, when water is heated at a suitable pressure, between 1 and 218 bar, its polarity decreases whilst the temperature increases.

The method preferred in accordance with the invention lies in using extraction by fluid in the supercritical state.

Thus, the invention relates firstly to a method for extracting a *Marsdenia cundurango* extract comprising terpinyl cinnamate compounds, said method comprising the following steps:

a) the bark and/or wood of *Marsdenia cundurango* creepers are/is collected, dried and then milled;
b) an extraction is performed with a fluid in the supercritical state;
c) the *Marsdenia cundurango* extract is recovered,
d) the extract obtained in step c) possibly is purified.

The extract obtained in step c) is pasty.

The fluid in the supercritical state is selected from carbon dioxide and argon, however in step b) it is preferred to use carbon dioxide in the supercritical state.

Step d) of purifying the extract obtained in step c) can be performed by any technique known to a person skilled in the art and in particular by chromatography or molecular distillation.

In accordance with a preferred embodiment of the method
  the extraction temperature is between 35 and 100° C., advantageously between 40 and 80° C., and preferably between 45 and 55° C.
  the pressure within the extractor is between 160 and 500 bar and preferably between 200 and 260 bar.
  the mass ratio of solvent (carbon dioxide) relative to the amount of first material used is between 10 and 70, advantageously between 25 and 55, and preferably between 35 and 45.

In a more preferred embodiment of the method according to the invention, the extraction in step b) is performed at a temperature of approximately 50° C. and a pressure of approximately 230 bar within the extractor so as to obtain an apolar extract in step c).

In yet a further, preferred embodiment, the *Marsdenia cundurango* extract obtained from the method according to the invention contains at least 10% by weight of terpinyl cinnamate compounds.

In a very preferred embodiment according to the invention, at least one apolar co-solvent is also used in step b).

Apolar co-solvents that can be used are preferably agro-sourced solvents, such as vegetable oils, acid esters and long- or short-chain alcohols, such as ethyl acetate, ethyl lactate, ethyl propionate, isopropyl palmitate, ethyl oleate, methyl stearate, oleyl oleate, triethyl citrate, glycerol caprylate/caprate triglyceride, or agro-sourced hydrocarbons comprising between 10 and 14 carbon atoms (C10 to C14), or a combination of these solvents.

The co-solvent is more preferably isopropyl palmitate or glycerol caprylate/caprate triglyceride, preferably glycerol caprylate/caprate triglyceride.

In this advantageous embodiment according to the invention, the action of the fluid in the supercritical state in step b) of the method is intensified by the co-solvent, such as a fatty acid such as glycerol caprylate/caprate triglyceride or isopropyl palmitate, preferably glycerol caprylate/caprate triglyceride, used as a solvent and liquid carrier cosmetically acceptable for the compounds of interest. The solvent is preferably an agro-sourced solvent. The term "agro-sourced" means molecules originating entirely or partially from biomass, these solvents moreover being renewable carbon compounds.

Thus, the method is advantageously performed in accordance with eco-extraction criteria using an apolar agro-sourced co-solvent in order to obtain the compounds of interest in a facilitated way, i.e. without the need for a subsequent purification step in order to eliminate the extraction solvents. In fact, the supercritical fluid evaporates spontaneously and the co-solvent is used as a liquid carrier that can be used directly in cosmetics.

Thus, the method advantageously comprises the steps:

a. cryo-milling of the bark and/or wood dried previously, then b. extraction by carbon dioxide in the supercritical state and in the presence of a co-solvent, such as glycerol caprylate/caprate triglyceride, then c. recovery of the extract in liquid form and possibly d. purification of the extract.

The invention relates secondly to a *Marsdenia cundurango* creeper bark and/or wood extract obtained by the method according to the invention.

In one embodiment the *Marsdenia cundurango* creeper bark and/or wood extract obtained by the method is pasty and comprises terpinyl cinnamate compounds in a concentration of at least 10% by weight of the total weight of the extract.

Under the conditions of use of carbon dioxide in the supercritical state alone, the method according to the invention makes it possible to obtain a pasty extract. As indicated in example 2, it has a content of molecules of interest (terpinyl cinnamate compounds) of at least 10% by weight of the total weight of the extract. The extract can also be dried and purified in order to obtain a content of molecules of interest up to 100% by weight of the total weight of the extract. This extract can then be diluted, under the conditions described in the preferred embodiment according to the invention, for cosmetic use.

In another preferred embodiment of the invention, when the extract is performed with the aid of a fluid in the supercritical state and at least one co-solvent, the *Marsdenia cundurango* creeper bark and/or wood extract is in liquid form and comprises terpinyl cinnamate compounds in a concentration of from 0.5% to 2% by weight of the total weight of the extract.

In a more preferred embodiment of the invention, the terpinyl cinnamate compounds of the extract are of following general formula I:

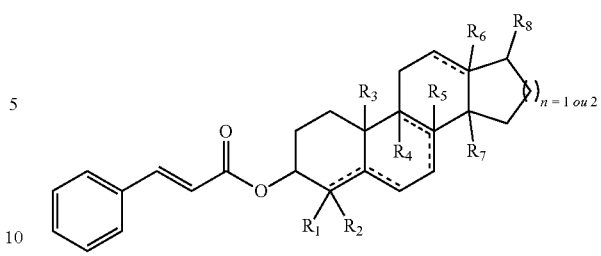

in which:

the radicals R1, R2, R3, R4, R5, R6 and R7 represent protons, methyls or saturated or non-saturated oxidised or non-oxidised alkyl chains, the radical R8 represents an oxidised or non-oxidised, saturated or non-saturated, cyclic or non-cyclic alkyl group, the dotted lines illustrate the potential presence of an unsaturation at this position.

In an even more preferred embodiment of the invention, the terpinyl cinnamate compounds are, respectively, β-amyrin cinnamate, 24-methylene cycloartanyl cinnamate, butyrospermyl cinnamate, cycloartenyl cinnamate and cyclofontumienyl cinnamate.

The proportion of terpinyl cinnamate compounds, depending on the origin of the *Marsdenia cundurango* creeper used, obtained from the bark and/or wood, is as follows:

19.4 to 35.7% butyrospermyl cinnamate,
13.2 to 24.6% cycloartenyl cinnamate,
16.9 to 31.5% β-amyrin cinnamate,
25.6 to 25.6% 24-methylene cycloartanyl cinnamate,
2.8 to 5.2% cyclofontumienyl cinnamate.

The condurango extract according to the invention is preferably obtained from *Marsdenia cundurango* creeper bark as starting material. The extract obtained is of the apolar type.

The *Marsdenia cundurango* creeper bark, collected and dried, preferably originates from South America. It can originate in particular from the equator, Peru or Colombia.

If the extract obtained by the method according to the invention is liquid, or advantageously comprises terpinyl cinnamate compounds at a concentration of from 0.5% to 2% by weight of the total weight of the extract and comprises the terpinyl cinnamate compounds, the other apolar compounds in trace form, and the extraction co-solvent. This concentration of compounds of interest can also be concentrated in liquid medium after purification by microfiltration, ultrafiltration and/or nanofiltration in order to concentrate the content of terpinyl cinnamate compounds in the extract as compared to the other compounds also extracted.

In a preferred embodiment the liquid extract in accordance with the invention originates from *Marsdenia cundurango* creeper bark.

The invention also relates to the extract originating from *Marsdenia cundurango* creeper bark and/or wood comprising terpinyl cinnamate compounds and able to be obtained by the method according to the invention.

The invention relates thirdly to a cosmetic composition comprising, as active agent, an effective amount of a *Marsdenia cundurango* extract and a physiologically acceptable excipient.

In a preferred embodiment of the invention, the extract is obtained solely from *Marsdenia cundurango* creeper bark.

In a preferred embodiment of the invention, the *Marsdenia cundurango* extract is present in the composition at a concentration of from 0.001 to 10% by weight in relation to the total weight of the composition, preferably from 0.01 to 5.0% by weight in relation to the total weight of the composition, and even more preferably from 0.01 to 2.0% by weight in relation to the total weight of the composition.

The compositions according to the invention are intended more particularly for topical administration. These compositions must therefore contain a cosmetically acceptable medium, that is to say one that is compatible with the skin and the appendages, and cover all cosmetic galenic forms. These compositions in particular can be in the form of creams, oil-in-water emulsions or multiple water-in-oil emulsions, solutions, suspensions, gels, milks, lotions, sticks, or powders, and can be suitable for application to the skin, the lips and/or the appendages. These compositions comprise the excipients necessary for their formulation, such as solvents, thickeners, diluents, surfactants, anti-oxidants, colourants, preservatives, perfumes. They can be used as a care product and/or as a skin make-up product.

The compositions according to the invention also comprise any additive commonly used in the envisaged field of application as well as the adjuvants necessary for their formulation, such as solvents, thickeners, diluents, anti-oxidants, colourants, solar filters, self-tanning agents, pigments, charges, preservatives, perfumes, odour-absorbers, cosmetic or pharmaceutical active agents, essential oils, vitamins, essential fatty acids, surfactants, film-producing polymers, etc.

L'INCI Dictionary & Handbook ("International Nomenclature of Cosmetic Ingredients 13th Ed. 2010) published by "the Personal Care Products Council, Inc.", Washington, D.C.) describes a wide range, without limitation, of cosmetic ingredients habitually used in the skincare industry, which are suitable for use as additional ingredients in the compositions according to the present invention.

Non-limiting examples of these classes of additional ingredients include: healing agents, anti-ageing agents, anti-wrinkle agents, anti-atrophy agents, hydrating agents, softening agents, keratolytic agents, anti-free radical agents, anti-seborrheic agents, anti-dandruff agents, agents modulating skin differentiation, proliferation or pigmentation, penetration accelerating agents, desquamation agents, agents which stimulate or inhibit the synthesis of melanin, bleaching agents, depigmentation agents or lightening agents, pro-pigmentation agents, self-tanning agents, NO-synthase-inhibiting agents, antioxidant agents, free radical trapping and/or anti-atmospheric pollution agents, anti-glycation agents, firming agents, agents stimulating the synthesis of dermal or epidermal macromolecules and/or agents capable of preventing or inhibiting their degradation, collagen synthesis stimulating agents, elastin synthesis stimulating agents, decorin synthesis stimulating agents, laminin synthesis stimulating agents, defensin synthesis stimulating agents, chaperone synthesis stimulating agents, aquaporin synthesis stimulating agents, hyaluronic acid synthesis stimulating agents, agents stimulating the synthesis of lipids and of components of the stratum corneum (ceramides, fatty acids, etc.), collagen degradation inhibiting agents, elastin degradation inhibiting agents, fibroblast proliferation stimulating agents, keratinocyte proliferation stimulating agents, adipocyte proliferation stimulating agents, melanocyte proliferation stimulating agents, keratinocyte differentiation stimulating agents, adipocyte differentiation stimulating agents, acetylcholinesterase inhibiting agents, glycosaminoglycan synthesis stimulating agents, DNA repair agents, DNA protection agents, anti-itch agents, agents for the treatment and/or care of sensitive skin, firming agents, anti-stretch mark agents, astringent agents, sebum production regulating agents, dermo-relaxant agents, re-epithelialisation stimulating agents, cytokine growth factors, agents acting on the capillary circulation and/or microcirculation, vascular permeability inhibiting agents, agents acting on cell metabolism, agents intended for improving the dermo-epidermal junction, agents inducing the growth of cranial hair and/or body hair, agents inhibiting or slowing the growth of cranial hair and/or body hair, myorelaxant agents, anti-pollution and/or anti-radical agents, lipolysis stimulating agents, slimming agents, anti-cellulite agents, agents acting on the cell metabolism, cleaning agents, hair styling agents, hair growth stimulants, sunscreens, sunblocks, makeup agents, detergents, emulsifying agents, emollients, organic solvents, antiseptic agents, deodorant active agents, physiologically acceptable media, surfactants, abrasive agents, absorbents, aesthetic components such as perfumes, pigments, colouring agents, dyes and natural dyes, essential oils, texture agents, cosmetic astringents, anti-foaming agents, antioxidants, ligands, biological additives, enzymes, enzymatic inhibitors, enzymatic inducers, coenzymes, chelating agents, plant extracts and plant derivatives, essential oils, marine extracts, agents originating from a biofermentation and/or biotechnology process, mineral salts, cellular extracts, sunscreens (organic or mineral photoprotective agents which are active against ultraviolet A and/or B radiation), ceramides, peptides, buffers, volume agents, chelating agents, chemical additives, dyes, cosmetic biocides, denaturing agents, film-producing agents such as polymers for enhancing film-producing properties and substantivity of the composition, quaternary derivatives, substantivity increasing agents, opacifiers, pH adjusting and regulating agents (example, triethanolamine), propellants, reducing agents, sequestering agents, skin bleaching and/or lightening agents, skin conditioning agents (i.e., humectants, including miscellaneous and occlusive), moisture retaining substances, alpha hydroxyl acids, beta hydroxyl acids, hydrating agents, epidermal hydrolytic enzymes, soothing and/or healing agents, skin treating agents, anti-wrinkle agents, agents capable of reducing or treating bags under the eyes, exfoliation agents, thickeners, softeners, gelling polymers, vitamins and their derivatives, wetting agents, peeling agents, soothing agents, lignans, preservatives (antifungal agents, fungistatic agents, bactericidal agents, bacteriostatic agents, i.e. phenoxyethanol and parabens), anti-UV agents, viscosity modifying agents, non-volatile solvents, beading agents, anti-perspiration agents, depilatory agents, perfumed water, skin restructuring agent, excipients, fillers, minerals, anti-irritation agents, insect repellent agents, lubricants, pigments or dyes, hypopigmentation agents, photo-stabilising agents, and mixtures thereof, provided that they are physically and chemically compatible with the other ingredients of the composition and especially with the active substances of the present invention.

In addition, the nature of these additional ingredients must not unacceptably change the benefits of the active ingredients of the invention. These additional ingredients can be synthetic or natural, for example plant extracts or extracts originating from a biofermentation process.

Such additional ingredients can also be chosen in accordance with their chemical composition from the group comprising: amino sugars, glucosamine, D-glucosamine, N-acetyl glucosamine, N-acetyl-D-glucosamine, mannosamine, N-acetyl mannosamine, galactosamine, N-acetyl galactosamine, vitamin B3 and derivatives thereof, niacinamide, sodium dehydroacetate, dehydroacetic acid and salts thereof, phytosterols, salicylic acid compounds, hexamidines, dihydroxyproline of dialkanoyl compounds, soybean extracts and derivatives, equol, isoflavones, flavonoids, phytantriol, farnesol, geraniol, bisabolol, peptides and derivatives thereof, di-, tri-, tetra-, penta- and hexapeptides and derivatives thereof, lys-thr-thr-lys-ser, palmitoyl-lys-thr-thr-lys-ser, carnosine, N-acyl amino acid compounds, retinoids, retinyl propionate, retinol, retinyl palmitate, retinyl acetate, retinal, retinoic acid, water-soluble vitamins, ascorbates, vitamin C, glucoside ascorbyl, palmitate ascorbyl, magnesium ascorbyl phosphate, sodium ascorbyl phosphate, vitamins and salts and derivatives thereof, provitamins and salts and derivatives thereof, ethyl panthenol, vitamin B and derivatives thereof, vitamin B1, vitamin B2, vitamin B6, vitamin B12, vitamin K and derivatives thereof, pantothenic acid and derivatives thereof, pantothenyl ethyl ether, panthenol and derivatives thereof, ethyl panthenol, dexpanthenol, biotin, amino acids and salts and derivatives thereof, water-soluble amino acids, asparagine, alanine, indole, glutamic acid, water-insoluble vitamins, vitamin A, vitamin E, vitamin F, vitamin D and compounds thereof, mono-, di- and triterpenoids, beta-ionol, cedrol and derivatives thereof, water-insoluble amino acids, tyrosine, tryptamine, particulate materials, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, ketoacids, pyruvic acid, phytic acid, lysophosphatidic acid, stilbenes, cinnamates, resveratrol, kinetin, zeatin, dimethylaminoethanol, natural peptides, soybean peptides, salts of acid sugars, manganese gluconate, zinc gluconate, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, alcohols of terpene, allantoin, bisabolol, dipotassium glycyrrhizinate, acid of glycerol, sorbitol, pentaerythritol, pyrrolidone and salts thereof, dihydroxyacetone, erythrulose, glyceraldehyde, tartaraldehyde, clove essence, menthol, camphor, eucalyptus essence, eugenol, menthyl lactate, hamamelis distillate, eicosene and vinyl pyrrolidone copolymer, iodopropyl butylcarbamate, a polysaccharide, an essential fatty acid, a salicylate, a glycyrrhetinic acid, carotenoids, ceramides and pseudo-ceramides, a complex lipid, oils of natural origin in general such as shea butter, apricot oil, onager oil, prune oil, palm oil, monoi oil, kahai oil, hydroquinone, HEPES, procysteine, β-octanoyl-6-D-maltose, disodium salt of methyl glycine diacetic acid, steroids such as diosgenin and the derivatives of DHEA, DHEA dehydroepiandrosterone and/or a chemical or biological precursor or derivative, N-ethylcarbonyl-4-para-aminophenol, blueberry extracts, phytohormones, *Saccharomyces cerevisiae* yeast extracts, extracts of algae, soybean, lupine, corn and/or pea, alverine and salts thereof, in particular alverine citrate, ruscus and horse chestnut extracts and combinations thereof, a metalloproteinase inhibitor, the *Schinus molle* extracts.

The following are noted by way of example:
the peptides known commercially by the name MATRIXYL®, ARGIRELINE®, CHRONOGEN™, LAMINIXYL IS™, PEPTIDE Q10™, COLLAXYL™ (brevet FR2827170, ASHLAND®), PEPTIDE VINCI 01™ (patent FR2837098, ASHLAND®), PEPTIDE VINCI 02™ (patent FR2841781, ASHLAND®), ATPeptide™ (patent FR2846883, ASHLAND®) or the synthetic peptide of sequence Arg-Gly-Ser-NH$_2$, sold under the name ATPeptide™ by ASHLAND®;

the extract of *Artimia salina*, sold under the name GP4G™ (FR2817748, ASHLAND®);
vegetable peptide extracts, such as extracts of flax (Lipigénine™, patent FR2956818, ASHLAND®), extracts of soya, wheat, vine, rape, flax, rice, corn, pea, cacao;
the extracts of yeasts, for example Dynagen™, (patent FR2951946, ASHLAND®) or Actopontine™ (patent FR2944526, ASHLAND®);

In any case, a person skilled in the art will ensure that these adjuvants and their proportions are selected so as not to adversely affect the advantageous properties sought in the composition according to the invention.

A fourth object according to the invention relates to the cosmetic use of a composition according to the invention for improving the barrier function of the skin, for improving protection against toxins, for improving the detoxification of the skin, and for fighting against the appearance of the signs of ageing and reducing the signs of ageing.

The skin is an organ of which the upper part, the stratum corneum, plays the role of a protective physical barrier with respect to the external environment. This barrier role, known more commonly as "barrier function of the skin" is of major importance in the protection against external agents having a negative effect on the skin, such as toxins.

Examples of toxins, in the sense of the invention, include environmental atmospheric pollutants, any solid or solubilised toxic substance able to come into contact with the skin, and toxins produced by living organisms, such as bacteria or fungi.

The use of a composition according to the invention, comprising an effective amount of a condurango extract, and preferably a *Marsdenia cundurango* creeper bark extract, makes it possible to better protect the skin against toxins, by promoting an improved epidermal differentiation and an improvement in the barrier function.

The use of the composition according to the invention thus contributes to the reduction in and fight against the appearance of the signs of skin ageing.

Autophagy is a lysosomal degradation pathway, allowing the elimination of toxins and degradation of intercellular components. Chaperone protein-mediated autophagy (CMA) is one of the selective forms of autophagy, characterised by the presence of LAMP2A (membrane protein associated with type 2A lysosomes). The substrates to be degraded (bonded to an hsc70 chaperone protein) bond to LAMP2 at the surface of the lysosome, enabling lysosomal translocation and their elimination. The amount of LAMP2A in the lysosomal membrane decreases with age, resulting in a failure of CMA activity.

Lastly, the invention relates fifthly to a cosmetic treatment method for increasing the expression of bitter taste receptors in skin cells, comprising topical application of a composition of the invention.

The family of receptors coupled to G proteins referred to as TAS2R is present in various organs, including the skin (Reszka E et al. Expression of bitter taste receptors in the human skin in vitro. J Clin Res Bioeth, 2015, 6:218), in which they could play a role in maintaining homeostasis.

Bitter taste receptors protect the organism against the ingestion of toxic substances, and control the metabolism, satiation, the treatment of ailments and integrated substances, and the detection of bacterial invasion. In particular, the activation of the receptor TAS2R38 in skin cells by different substances, including metabolites of plants and chemical substances, leads to a salting-out of calcium in the cytoplasm and to a depolarisation of the cellular membrane, inducing a salting-out of ATP. The activation of this receptor is associated with an improvement in skin barrier function (Walfle U et al. Expression and functional activity of the bitter taste receptors TAS2R1 and TAS2R38 in human keratinocytes. Skin Pharmacol Physiol. 2015; 28(3):137-46).

By way of example, preferred exemplary embodiments of the invention are described hereinafter.

The invention and advantages thereof will be better understood upon reading the description and studying non-limiting embodiments, which are summarised with reference to the accompanying figured, in which.

EXAMPLE 1: PREPARATION OF THE MARSDENIA CUNDURANGO BARK POWDER

Figure 1:
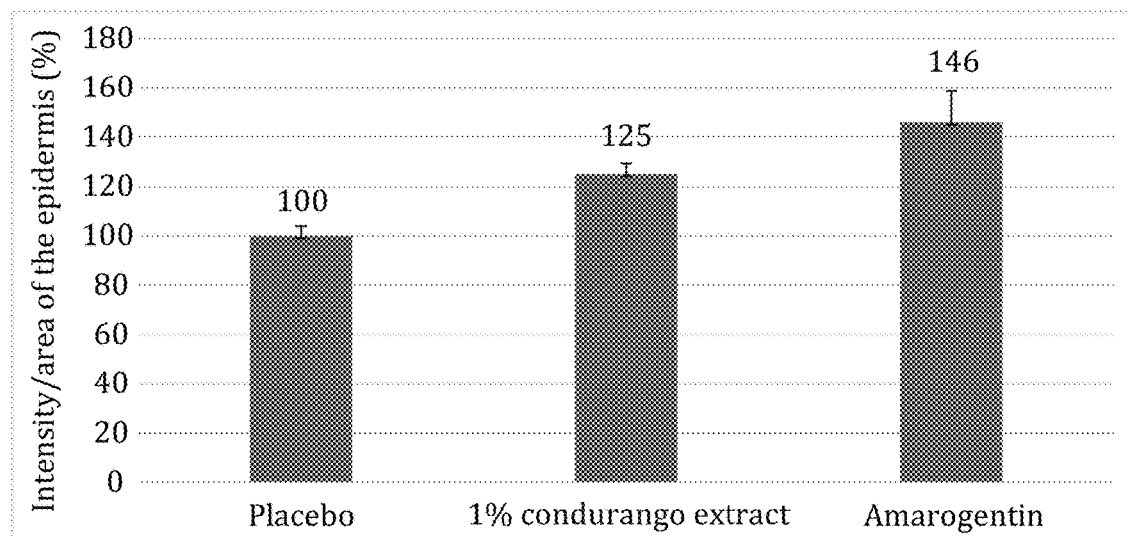
FIG. 1 (example 5) shows the quantification of the expression of bitter taste receptors (TAS2R38) in skin biopsies following treatment by a 1% condurango extract.

The applicants are currently in the process of applying for a search and commercialisation permit from the Colombian government so as to have access to Marsdenia cundurango genetic resources.

Marsdenia cundurango barks are harvested in Colombia, then dried in the sun or by a hot air flow, the temperature of which is between 40 and 70° C., so as to obtain a residual humidity content less than 10%. The barks are milled in a cutting mill comprising a 2 mm grating, which makes it possible to obtain a powder of which the particle size is between 100 and 800 µm, advantageously between 300 and 600 µm, and more preferably between 400 and 500 µm.

EXAMPLE 2: PREPARATION OF A CONDURANGO EXTRACT BY EXTRACTION WITH CARBON DIOXIDE IN THE SUPERCRITICAL STATE

The powder obtained in example 1 (1.0 kg) was placed in a stainless steel cartridge, and this cartridge was placed in a supercritical fluid extractor (SFE5, SEPAREX). The solvent used for extraction was carbon dioxide in the supercritical state. The solvent/first material ratio was 230 bar. The pressure within the extractor was 230 bar. The extraction temperature was 50° C.

The extraction yield was 0.2%, and the product obtained was pasty at ambient temperature.

A content of terpinyl cinnamates in the extract was approximately 10 to 20 mass %.

This first crude form of the extract corresponded to the definition of pasty extract according to the invention and was suitable for use in this form for preparing cosmetic compositions.

Purification a:

This first crude form of the extract was placed on a silica column of appropriate size for the mass of extract to be purified. The separation of the compounds of interest was performed by flash chromatography with a solvent gradient ranging from 100% heptane to a 9/1 (v/v) heptane/ethyl acetate mixture. The column was then rinsed, progressively increasing the proportion of ethyl acetate in the mobile phase to 100%. The content of the various collection tubes was analysed by thin-film chromatography so as to identify the tubes that contained the compounds of interest. The latter were amalgamated, then the solvents were eliminated on a rotary evaporator so as to obtain a fraction containing 100% terpinyl cinnamate compounds.

The proportion of terpinyl cinnamate compounds obtained was as follows:
30% butyrospermyl cinnamate,
21% cycloartenyl cinnamate,
23% β-amyrin cinnamate,
21% 24-methylenecycloartanyl cinnamate,
5% cyclofontumienyl cinnamate.

The elution zone of the compounds of interest made it possible to observe numerous elution peaks. Only 5 compounds described in the present invention were isolated and studied in detail. The extract thus likely contained other compounds of the same chemical family, because other polarity peaks similar to those of the described terpinyl cinnamates were observed. These compounds also had UV spectra close to the compounds of interest with in particular an absorption maximum close to 280 nm and a comparable mass spectrometry fragmentation.

Purification b:

The pasty $CO_2$ extract was purified by molecular distillation on a KDL1 wiped film distiller (UIC GmbH), in a high-vacuum atmosphere of $8 \times 10^1$ mbar and at a temperature of 250° C.

The obtained distillate contained 98% of terpinyl cinnamate compounds.

EXAMPLE 3: PREPARATION OF A CONDURANGO EXTRACT BY SUPERCRITICAL CARBON DIOXIDE EXTRACTION IN THE PRESENCE OF AN ISOPROPYL PALMITATE CO-SOLVENT

The powder obtained in example 1 (1.0 kg) was placed in a stainless steel cartridge, and this cartridge was placed in a supercritical fluid extractor (SFE5, SEPAREX). The solvent used for extraction was carbon dioxide in the supercritical state, in the presence of an apolar co-solvent constituted by isopropyl palmitate. The solvent/first material ratio was approximately 45, and the flow rate of isopropyl palmitate was 10 ml/minute. The pressure within the extractor was 230 bar. The extraction temperature was 50° C. The liquid extract thus obtained could be dried (dehydrated) over anhydrous sodium sulphate, then filtered. After filtration, 1.6 kg of liquid extract were obtained. The extraction yield was thus close to 160%.

The content of terpinyl cinnamate compounds in the liquid extract at ambient temperature was between 0.5 and 2 mass %.

EXAMPLE 4: PREPARATION OF A CONDURANGO EXTRACT BY SUPERCRITICAL CARBON DIOXIDE EXTRACTION IN THE PRESENCE OF A GLYCEROL CAPRYLATE/CAPRATE TRIGLYCERIDE CO-SOLVENT

The powder obtained in example 1 was placed in a stainless steel cartridge, and this cartridge was placed in a supercritical fluid extractor. The solvent used for extraction was carbon dioxide in the supercritical state in the presence of glycerol caprylate/caprate triglyceride as apolar co-solvent. The solvent/first material ratio was approximately 45, and the flow rate of the glycerol caprylate/caprate triglyceride was 10 ml/minute. The pressure within the extractor was 230 bar. The extraction temperature was 50° C. The extract thus obtained could be dried (dehydrated) over anhydrous sodium sulphate, then filtered. After filtration, 1.6 kg of liquid extract were obtained. The extraction yield was thus close to 160%.

The content of terpinyl cinnamate compounds in the extract was between 0.5 and 2 mass %.

EXAMPLE 5: EVALUATION OF THE EFFECTS OF A *MARSDENIA CUNDURANGO* EXTRACT ON THE EXPRESSION OF TAS2R38 RECEPTORS IN SKIN BIOPSIES

The objective of this study was to evaluate the effect of a treatment by a *Marsdenia cundurango* (condurango) bark extract on the expression of the bitter taste receptor TAS2R38 in human skin biopsies.

TAS2R38 receptors are characterised in this study by immunomarking and demonstrate the ability of the skin to react to different stimuli in its environment.

Protocol:

Human skin biopsies in culture were treated by the condurango extract obtained in example 4 and formulated to 1% (mass/mass) in a cream applied twice per day for 48 hours topically (20 μl/biopsy). Control biopsies received a placebo cream. The formulas used were conventional oil-in-water emulsions, produced from commonly used ingredients. Amarogentin, which is a bitter molecule present in gentian roots, was selected as TAS2R38 receptor activator and was applied as a positive experiment control (extra synthesis 100 μM). The biopsies were maintained in culture for 48 hours.

TAS2R38 receptors were then detected by immunomarking with the aid of a specific antibody.

This technique was performed on the basis of paraffin sections, incubated in the presence of the anti-TAS2R38 antibody (rabbit polyclonal antibody, Abcam). After one night of incubation followed by rinsings, the sections were incubated in the presence of the secondary anti-rabbit antibody coupled with a fluorophore (Alexa Fluor® 488, Invitrogen). The sections were then examined under epi-fluorescence microscope (Zeiss Axiovert 200M microscope). The expression of TAS2R38 was then observed and quantified at epidermis level.

Results:

As shown by FIG. 1, the treatment with the 1% condurango extract revealed an increase in the marking intensity of TAS2R38 in skin biopsies at 48 hours (+25%, very significant compared to the placebo).

Conclusion:

The application of the condurango extract made it possible to increase the expression of the bitter taste receptor TAS2R38 in skin biopsies.

EXAMPLE 6: EVALUATION OF THE EFFECTS OF A CONDURANGO EXTRACT ON THE EXPRESSION OF INVOLUCRIN IN SKIN BIOPSIES

The objective of this study was to evaluate the effect of a treatment by the condurango extract on the expression of involucrin, as differentiation protein, in the human epidermis.

Protocol:

Human skin biopsies in culture were treated with the condurango extract obtained in example 4 and formulated to 1% (mass/mass) in a cream, in accordance with the same protocol as in example 5. Control biopsies received a placebo cream. EGCG (epigallocatechin gallate, Sigma), a polyphenol extracted from green tea and known to increase the differentiation of epidermis cells, was selected as positive control for this experiment, diluted to 200 μg/ml. The biopsies were maintained in culture for 48 hours.

Involucrin was then detected by immunomarking with the aid of a specific antibody.

Figure 2:
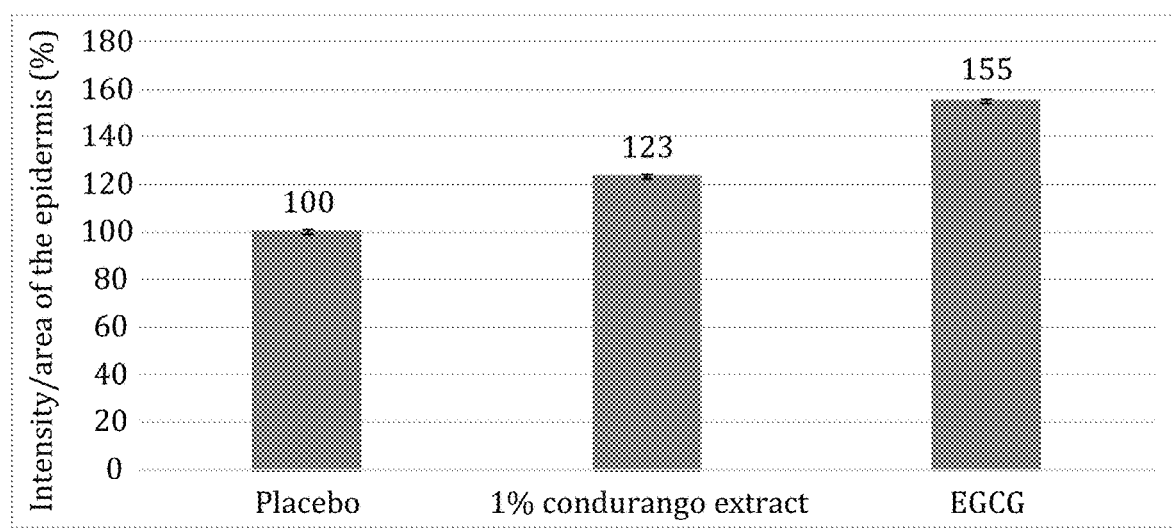
FIG. 2 (example 6) shows the quantification of the expression of involucrin in skin biopsies following treatment by a 1% condurango extract.

This technique was performed on paraffin skin sections, incubated in the presence of the anti-involucrin antibody (mouse monoclonal antibody, Novocastra). After 1 hour is incubation followed by rinsings, the sections were incubated in the presence of the secondary anti-mouse antibody coupled with a fluorophore (Alexa Fluor® 488, Invitrogen). The sections were then examined under epi-fluorescence microscope (Zeiss Axiovert 200M microscope). The expression of involucrin in the epidermis was then observed and quantified Results:

As shown by FIG. 2, the extract of 1% condurango led to an increase in the marking intensity of involucrin in biopsies treated over 48 hours (+23%, highly significant).

Conclusion:

This text ex vivo makes it possible to conclude a positive effect of the condurango extract on the expression of involucrin, in conjunction with the skin barrier function.

EXAMPLE 7: EVALUATION OF THE EFFECTS OF THE CONDURANGO EXTRACT ON THE EXPRESSION OF THE LAMP2 AUTOPHAGY MARKER AFTER MULTI-TOXIN STRESS IN SKIN BIOPSIES IN CULTURE

The objective of this study was to observe the effect of treatment by condurango on skin biopsies previously subjected to multi-toxin stress, brought about by incubating the biopsies with cigarette smoke.

The selected marker is the lysosomal membrane protein LAMP2A, which is involved in the process of autophagy, one of the main pathways of degradation of cellular waste.

Protocol:

Human skin biopsies in culture were placed in a sealed chamber saturated with cigarette smoke for 30 minutes. This stress was referred to as multi-toxic stress due to the cigarette smoke being composed of toxic molecules from different classes. After the stress, the biopsies were placed in culture and treated by the condurango extract obtained from example 4 and formulated to 1% (mass/mass) in a cream, as in example 5. Control biopsies without stress were incubated under the same conditions. EGCG (epigallocatechin gallate, Sigma), a polyphenol from green tea, was used as positive control for this experiment, diluted to 200 μg/ml.

At the end of this incubation, the protein LAMP2 was detected by immunomarking on skin biopsy sections.

This technique was performed on paraffin skin sections incubated in the presence of the anti-LAMP2 antibody (rabbit polyclonal antibody, Abcam) After 1 hour of incubation followed by rinsings, the sections were incubated in the presence of secondary anti-rabbit antibody coupled with a fluorophore (Alexa Fluor® 488, Invitrogen). The sections were then examined under epi-fluorescence microscope (Zeiss Axiovert 200M microscope). The expression of LAMP2 was then observed and quantified at epidermis level.

Figure 3:
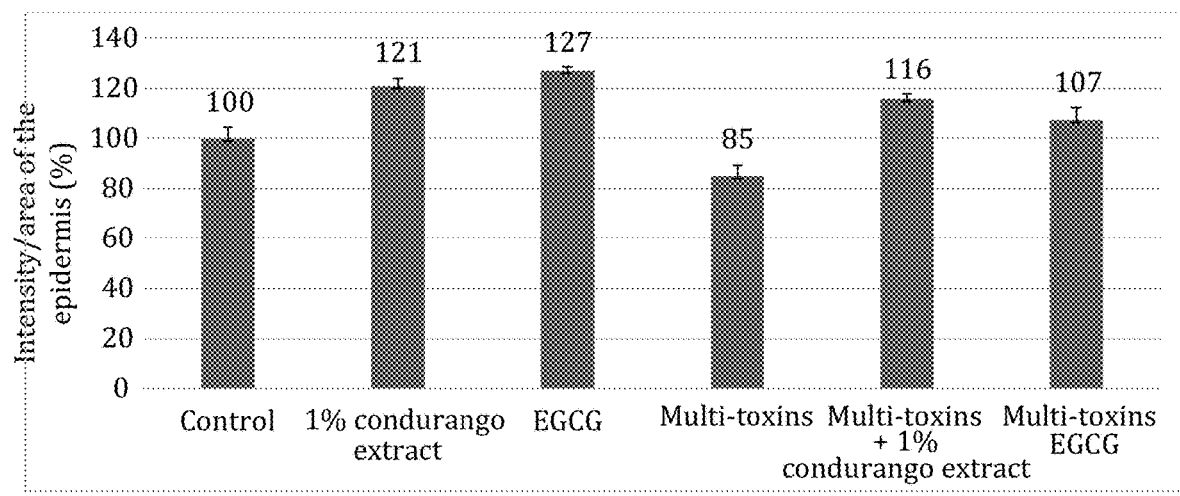
FIG. 3 (example 7) shows the quantification of the expression of the autophagy marker LAMP2 in skin biopsies exposed to multi-toxin stress, then to treatment by a 1% condurango extract.

Results:

As shown in FIG. 3, in the absence of stress, the treatment with 1% condurango extract led to a rise in the marking intensity of LAMP2 in the skin biopsies at 48 hours (+21%, very significant), close to that obtained with the positive control EGCG (+27, highly significant). The multi-toxic stress led to a reduction of LAMP2 (−15%, significant), whereas in the presence of condurango extract, an increase was observed, compensating for the effect of the stress (+36%, highly significant, compared to +26%, significant for the EGCG control).

Conclusion:

In the absence of stress, the condurango extract was favourable to proteostasis by increasing the expression of the LAMP2 autophagy marker. In the presence of a multi-toxic stress, the condurango extract was favourable to the elimination of damage induced by the stress in the skin biopsies.

EXAMPLE 8: EFFECT OF THE CONDURANGO STRESS ON THE SALTING-OUT OF INTERLEUKIN-6 BY SKIN BIOPSIES IN CULTURE SUBJECTED TO A STRESS BY THE SUBSTANCE P

The objective of this experiment was to study the effect of the condurango extract on skin biopsies subjected to a stress by the substance P. The substance P was the central mediator of neurogenic inflammation (inflammation mediated via the peripheral nervous system). The neuropeptide is involved in various processes, including acute or chronic inflammation, and the perception of pain or nociception. The effect of the stress, whether or not brought about in the presence of the condurango extract, was studied by measuring the salting-out of interleukin-6 (IL-6), a cytokine synthesised by skin cells and considered to be a nociceptive inflammation mediator (O'Donovan A et al. Clinical anxiety, cortisol and interleukin-6: evidence for specificity in emotion-biology relationships. Brain Behav Immun. 2010 October; 24(7): 1074-7).

Protocol:

Skin biopsies in culture were treated with the condurango extract obtained from example 4, formulated to 1% in a cream, as in example 5, with or without addition of substance P at $10^{-6}$ M in the culture medium.

After 48 hours of incubation, the culture medium of the biopsies was collected and the level of IL-6 was measured by ELISA.

Figure 4:
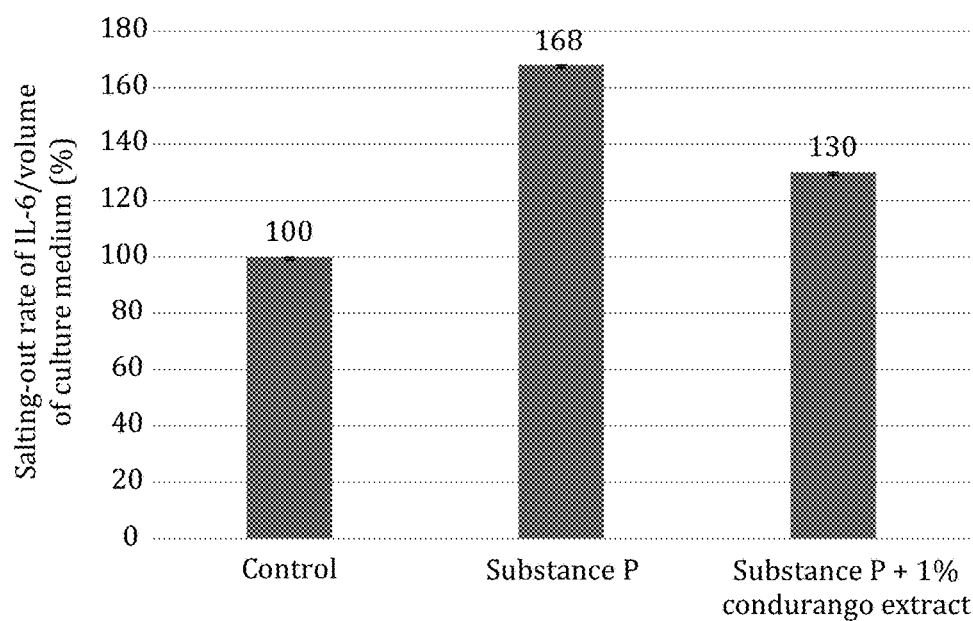
FIG. 4 (example 8) shows the quantification of the salting out of interleukin-6 by skin biopsies treated by a 1% condurango extract and subjected to a stress by the substance P.

Results:

As shown in FIG. 4, the stress caused by the substance P led to a rise in the level of IL-6 of +68% compared to the non-stressed control. The treatment by 1% condurango extract reduced the level of JIL-6 (+30% compared to the non-stressed control).

Conclusion:

The condurango extract made it possible to limit the neurogenic stress induced by the substance P in skin biopsies.

EXAMPLE 9: FORMULATION OF A HYDRATING MARINE EMULSION

| Ingredient/Commercial name | INCI name | % |
|---|---|---|
| Phase A | | |
| Purified water | Water/Aqua | Qs. 100 |
| Disodium EDTA | Disodium EDTA | 0.10 |
| Stabileze ™ QM polymer | PVM/MA Decadiene Crosspolymer | 0.50 |
| Lubrajel ™ Marine* hydrogel | Water/Aqua (and) Glycerol (and) Sodium PCA (and) Erythritol (and) Carrageenan (and) Xanthan Gum | 4.00 |
| Phase B | | |
| ProLipid ™ 141 lamellar Gel | Glyceryl Stearate (and) Behenyl Alcohol (and) Palmitic Acid (and) Stearic Acid (and) Lecithin (and) Lauryl Alcohol (and) Myristyl Alcohol (and) Cetyl Alcohol | 4.00 |
| Refined Shea Butter | *Butyrospermum Parkii* (Shea) Butter | 1.00 |
| Emulsynt ™ GDL ester | Glyceryl Dilaurate | 2.00 |
| Ceraphyl ™ ODS ester | Octyldodecyl Stearate | 2.00 |
| Ceraphyl SLK ester | Isodecyl Neopentanoate | 5.00 |
| Ceraphyl 368 ester | Ethylhexyl Palmitate | 3.00 |
| Belsil ™* PDM 20 | Trimethylsiloxyphenyl Dimethicone | 3.00 |
| Condurango extract according to example 4 | Marsdenia Condurango Bark Extract | 1.00 |
| Phase C | | |
| Sodium Hydroxide | Sodium Hydroxide | 0.13 |
| Purified water | Water/Aqua | 2.00 |
| Phase D | | |
| Optiphen ™ DP preservative | Propylene carbonate (and) Benzoic Acid (and) Dehydroacetic Acid (and) Propanediol | 1.00 |
| Optiphen OD preservative booster | Caprylyl Glycol | 0.50 |
| Phase E | | |
| Purified water | Water/Aqua | 10.00 |
| Natrosol ™ Plus 330 CS HMHEC | Cetyl Hydroxyethylcellulose | 0.10 |

-continued

| Ingredient/Commercial name | INCI name | % |
|---|---|---|
| Phase F | | |
| PF Mineral Defense 8509133 | Fragrance/Parfum (and) Butylphenyl methylpropional (Lilial) (and) Hydroxycitronellal | 0.20 |

Preparation Method:
1. In the main vessel, commence heating to 75° C. and add the ingredients of phase A one at a time, with mixing, until complete homogenisation is achieved.
2. In a second beaker, prepare phase B and heat to 75° C.
3. At 75° C., pour phase B into phase A and mix to complete homogenisation.
4. Premix phase C and add to the main vessel at 60° C.
5. At 45° C., add the ingredients of phase D, one at a time, whilst mixing until complete homogenisation is achieved after each ingredient.
6. In a separate beaker, prepare phase E: sprinkle Natrosol into water at ambient temperature and homogenise the mixture whilst heating to 60° C.
7. At 30° C., add phase E and mix well.
8. At ambient temperature, add phase F and mix well.
9. Stop at 25° C.
10. Appearance: White emulsion; pH: 4.8-5.3; Viscosity (DO): 25000-35000 cps (Brookfield RVT/Spindle B/5 RPM/1 minute/25° C.)
11. Preservation of the formula was validated by a double efficacy test after 28 days.

However, the preservatives were not optimised at their lowest efficacy level.

The invention claimed is:

1. A method for obtaining a *Marsdenia cundurango* extract comprising terpinyl cinnamate compounds, characterised in that the method comprises the following steps:
   a) collecting a bark and/or wood of *Marsdenia cundurango* creepers, drying, and then milling;
   b) extracting the milled *Marsdenia cundurango* creepers with a carbon dioxide in the supercritical state, at a temperature between 45 and 55° C. and at a pressure between 200 and 260 bar within the extractor to obtain a *Marsdenia cundurango* extract;
   c) recovering the *Marsdenia cundurango* extract; and
   d) optionally purifying the extract obtained in step c), wherein the terpinol cinnamate compounds are the following general formula I:

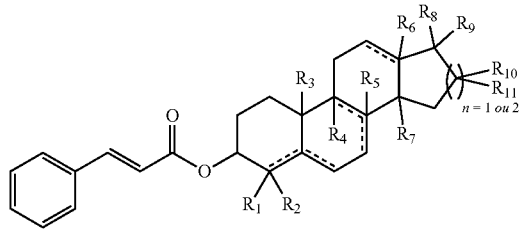

in which:
the radicals R1, R2, R3, R4, R5, R6 and R7 represent protons, methyls or saturated or nonsaturated oxidised or non-oxidised alkyl chains,
the radicals R8, R9, R10 and R11 represent protons, methyls, or oxidised or non-oxidised, saturated or non-saturated, cyclic or non-cyclic alkyl groups,
the dotted lines illustrate the potential presence of an unsaturated bond at this position, and wherein the terpinyl cinnamate compounds comprise β-amyrin cinnamate, 24-methylene cycloartanyl cinnamate, butyrospermyl cinnamate, cycloartenyl cinnamate and cyclofontumienyl cinnamate.

2. The method according to claim 1, characterised in that the *Marsdenia cundurango* extract contains at least 10% by weight of terpinyl cinnamate compounds.

3. The method according to claim 1, characterised in that in step b) at least one apolar co-solvent is also used.

4. The method according to claim 3, characterised in that the said at least one apolar co-solvent is an agro-sourced solvent selected from vegetable oils, acid esters and long- or short-chain alcohols, selected from ethyl acetate, ethyl lactate, ethyl propionate, isopropyl palmitate, ethyl oleate, methyl stearate, oleyl oleate, triethyl citrate, glycerol caprylate/caprate triglyceride, or agro-sourced C10 to C14 hydrocarbons, or a combination of these solvents.

5. The method according to claim 1, characterised in that the extract is pasty and the terpinyl cinnamate compounds in the extract are present in a concentration of at least 10% by weight of the total weight of the extract.

6. The method according to claim 3, characterised in that the extract is in liquid form and the terpinyl cinnamate compounds in the extract are present in a concentration of from 0.5% to 2% by weight of the total weight of the extract.

7. The method according to claim 6, characterised in that the extract originates from the *Marsdenia cundurango* creeper bark.

8. A cosmetic composition, comprising, as an active agent, an effective amount of a *Marsdenia cundurango* extract obtained by the method according to claim 6, and a physiologically acceptable excipient, and wherein the cosmetic composition is in a cosmetic galenic form selected from creams, oil-in-water emulsions, multiple water-in-oil emulsions, milks lotions or sticks wherein the terpinyl cinnamate compounds are the following general formula I:

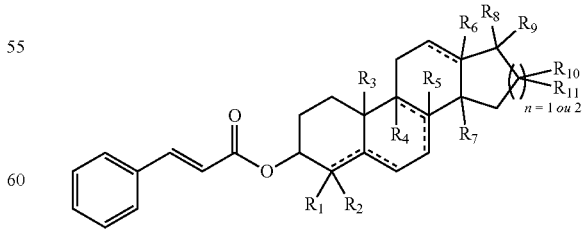

in which:
the radicals R1, R2, R3, R4, R5, R6 and R7 represent protons, methyls or saturated or nonsaturated oxidised or non-oxidised alkyl chains, the radicals R8, R9, R10 and R11 represent protons, methyls, or oxidised or non-oxidised, saturated or non-saturated, cyclic or non-cyclic alkyl groups, the dotted lines illustrate the potential presence of an unsaturated bond at this position, and wherein the terpinyl cinnamate compounds comprise β-amyrin cinnamate, 24-methylene cycloartanyl cinnamate, butyrospermyl cinnamate, cycloartenyl cinnamate and cyclofontumienyl cinnamate.

9. The composition according to claim 8, characterised in that the *Marsdenia cundurango* extract is present in the composition at a concentration of from 0.01 to 10% by weight in relation to the total weight of the composition.

10. The composition according, to claim 8, characterised in that it is formulated for topical application to skin.

11. A method of cosmetic treatment comprising topically applying the cosmetic composition of claim 8 to skin wherein the cosmetic treatment is for improving the barrier function of the skin, for improving protection against toxins, for increasing the detoxification capabilities of the skin and/or for reducing the signs of ageing.

12. A method of cosmetic treatment comprising topically applying the cosmetic composition of claim 8 to the skin wherein the cosmetic treatment is for increasing the expression of bitter taste receptors in skin cells.

13. The composition according to claim 8, characterised in that the *Marsdenia cundurango* extract is present in the composition at a concentration of from 0.01 to 5% by weight in relation to the total weight of the composition.

* * * * *